United States Patent [19]

Wootton et al.

[11] 4,298,745
[45] Nov. 3, 1981

[54] HYDANTOIN DERIVATIVES

[75] Inventors: Gordon Wootton, Herts; Richard W. Moore, Harlow, both of England

[73] Assignee: Beecham Group Limited, England

[21] Appl. No.: 95,339

[22] Filed: Nov. 19, 1979

Related U.S. Application Data

[63] Continuation of Ser. No. 4,897, Jan. 19, 1979, abandoned.

[30] Foreign Application Priority Data

Jan. 23, 1978 [GB] United Kingdom ............... 02694/78
May 12, 1978 [GB] United Kingdom ............... 19232/78

[51] Int. Cl.³ .................................. C07D 233/54
[52] U.S. Cl. .................................. 548/313; 424/273 R
[58] Field of Search ..................... 548/313; 424/273 R

[56] References Cited

U.S. PATENT DOCUMENTS 4,147,796   4/1979   Wootton ............................ 548/313

FOREIGN PATENT DOCUMENTS 2724948  12/1977  Fed. Rep. of Germany ...... 548/313

Primary Examiner—Henry H. Jiles
Assistant Examiner—Jane T. Fan

Attorney, Agent, or Firm—Jacobs & Jacobs

[57] ABSTRACT

Compounds of the formula 1:

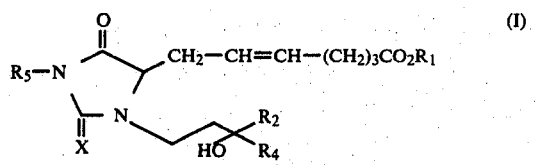

wherein:
X is O or S;
$R_1$ is hydrogen, or $CO_2R_1$ represents an ester group in which the $R_1$ moiety contains from 1-12 carbon atoms;
$R_2$ is hydrogen or $C_{1-4}$ alkyl;
$R_4$ is $C_{1-9}$ alkyl, $C_{3-8}$ cycloalkyl or $C_{3-8}$ cycloalkyl-$C_{1-6}$ alkyl; or
$R_2$ and $R_4$ taken with the carbon atom to which they are joined represent a $C_{5-8}$ cycloalkyl group; and
$R_5$ is $C_{1-6}$ alkyl; and salts thereof, having similar activity to natural prostaglandins, a process for their preparation, intermediates useful in that process and pharmaceutical compositions containing them.

15 Claims, No Drawings

HYDANTOIN DERIVATIVES

CROSS-REFERENCE

This is a continuation, of Ser. No. 004,897 filed Jan. 19, 1979, now abandoned.

This invention relates to novel compounds having pharmacological activity, to a process for their preparation, to intermediates useful in that process and to pharmaceutical compositions containing them.

German Offenlegungsschrift No. 2,724,948 discloses that compounds of the general formula (A):

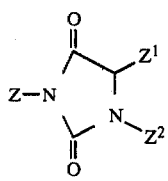

wherein:
Z is hydrogen or alkyl;
one of $Z^1$ and $Z^2$ is a group $-CH_2-X-X^1-X^2$ in which X is phenylene, $-C\equiv C-$, cis- or trans- $-CH=CH-$ or $-CH_2-CQ_2-$, where each radical Q independently of the other is hydrogen and/or alkyl or the two radicals Q together are $C_{4-6}$ alkylene, $X^1$ is a covalent bond or a straight or branched $C_{1-6}$ alkylene chain, in which one methylene group is optionally substituted by an oxa $(-O-)$ group, with the proviso that at least one carbon atom separates the oxa group from a $-C\equiv C-$, $-CH=CH-$ or CO group, and $X^2$ is tetrazolyl, carboxyl, carboxamide, hyroxymethylene and/or alkoxycarbonyl;
and the other one of $Z^1$ and $Z^2$ is a group $-Y-Y^1-Y^2-Y^3$ in which Y is $-CR_2-CH_2-$, where each radical R independently of the other is hydrogen and/or methyl,
Y is carbonyl, methylene, methylene substituted by a hydroxy group or methylene substituted by a hydroxy and an alkyl group,
$Y^2$ is a covalent bond or straight-chain or branched $C_{1-7}$ alkylene optionally substituted on the carbon atom adjacent to $Y^1$ by one or two mutually independent alkyl, bicycloalkyl or cycloalkyl groups,
$Y^3$ is hydrogen, hydroxy, $C_{1-7}$ (preferably $C_{1-4}$) alkoxy, cycloalkyl, bicycloalkyl, phenyl, benzyl, phenoxy, or benzyloxy, where each phenyl, benzyl, phenoxy or benzyloxy group may be substituted in the benzene ring by one or more hydroxy, halogen, nitro, amino, acylamino, alkenyl, alkoxy, phenyl and/or alkyl groups, which themselves may be substituted by one or more halogens, or
Y is a bond, $-CH_2-$ or $-CH_2.CH_2-$ and
$Y^1$, $Y^2$ and $Y^3$ together are cycloalkyl which is substituted by a hydroxy group which is preferably separated by 3 carbon atoms from the hydantoin ring, have similar pharmacological activity to natural prostaglandins.

We have now found that a specific narrow class of compounds which falls largely within this general disclosure has surprisingly improved bronchodilation activity relative to the compound which was specifically highlighted in the above Offenlegungsschrift for this utility.

Accordingly the present invention provides a compound of the formula (I):

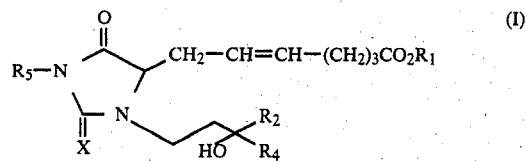

wherein:
X is O or S;
$R_1$ is hydrogen, or $CO_2R_1$ represents an ester group in which the $R_1$ moiety contains from 1-12 carbon atoms;
$R_2$ is hydrogen or $C_{1-4}$ alkyl;
$R_4$ is $C_{1-9}$ alkyl, $C_{3-8}$ cycloalkyl or $C_{3-8}$ cycloalkyl -$C_{1-6}$ alkyl; or
$R_2$ and $R_4$ taken with the carbon atom to which they are joined represent a $C_{5-8}$ cycloalkyl group; and
$R_5$ is $C_{1-6}$ alkyl; and salts thereof.

Particularly suitable compounds within formula (I) include those where X is O. Suitable examples of $R_1$ include hydrogen, methyl, ethyl, n- and iso-propyl, n-, sec- and tert-butyl, phenyl, benzyl, tolyl and the like while normally hydrogen or $C_{1-6}$ alkyl groups are preferred.

Suitable examples of $R_2$ include hydrogen, methyl and ethyl. More suitably $R_2$ is hydrogen or methyl, preferably methyl.

Suitably groups $R_4$ when $R_4$ is an alkyl group include $C_{4-9}$ alkyl groups. Such $C_{4-9}$ alkyl groups may be straight chain alkyl groups, such as n-butyl, n-pentyl, n-hexyl and n-heptyl, or may be alkyl groups branched by one or two methyl groups (at the same or different carbon atoms). Thus for example, $R_4$ may be a group $CH_2R_7$, $CH(CH_3)R_7$ or $C(CH_3)_2R_7$, wherein $R_7$ is a straight chain alkyl group such that the carbon content of the resultant group $R_4$ is 4 to 9.

In general preferred groups $R_4$ when $R_4$ is an alkyl group include straight chain pentyl, hexyl and heptyl groups. Of these, straight chain hexyl is often the most useful. Other preferred groups $R_4$ include groups $CH(CH_3)R_7$ and $C(CH_3)_2R_7$ wherein $R_7$ is straight chain butyl, pentyl or hexyl.

Other suitable examples of $R_4$ when $R_4$ is an alkyl group include the lower alkyl groups, that is when $R_4$ is a $C_{1-4}$ alkyl group.

When $R_4$ is or contains a $C_{3-8}$ cycloalkyl moiety, the moiety may be cyclopropyl. The moiety may also be a $C_{5-8}$ cycloalkyl moiety such as a cyclohexyl moiety. Examples of suitable $C_{1-6}$ alkyl moieties when $R_4$ is a $C_{3-8}$ cycloalkyl-$C_{1-6}$ alkyl group include methyl, ethyl, propyl, butyl, and pentyl.

Also, $R_2$ and $R_4$ taken with the carbon atom to which they are joined can represent a $C_{5-8}$ cycloalkyl group, such as the cyclohexyl group.

Suitable examples of $R_5$ include methyl, ethyl, n- and iso-propyl, n-, sec- and tert-butyl. More suitably $R_5$ is methyl or ethyl, preferably methyl.

The compounds of the formula (I) may form conventional salts. Such salts include those with alkali and alkaline earth metals, suitably sodium and potassium, and ammonium and substituted ammonium salts.

From the aforesaid it will be seen that one particularly suitable group of compounds within formula (I) is of formula (II):

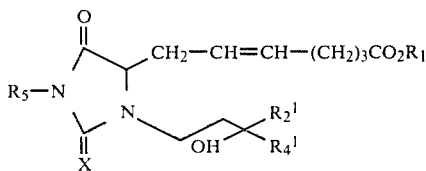

wherein:
X, $R_1$ and $R_5$ are as defined in formula (I);
$R^1_2$ is hydrogen, methyl or ethyl;
$R^1_4$ is $C_{1-9}$ alkyl; and salts thereof.

In formula (II) suitably X is O.

$R^1_2$ is more suitably hydrogen or methyl, preferably methyl.

While $R^1_4$ may be a $C_{1-9}$ alkyl group, it is normally a $C_{4-9}$ alkyl group. In such cases suitable and preferred straight chain and branched groups $R^1_4$ include thos previously described as suitable and preferred for the group $R_4$ when $R_4$ is a $C_{4-9}$ alkyl group. Such preferred groups $R^1_4$ include straight chain pentyl, hexyl, and heptyl, and of these normally the most useful is straight chain hexyl. Other preferred groups $R^1_4$ include $CH(CH_3)R^1_7$ and $C(CH_3)_2R^1_7$ wherein $R^1_7$ is straight chain butyl, pentyl or hexyl.

Suitably $R_5$ is methyl or ethyl, preferably methyl.

A further group of compounds within formula (I) of interest is of formula (III):

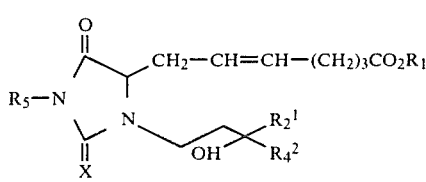

wherein:
X, $R_1$ and $R_5$ are as defined in formula (I):
$R^1_2$ is hydrogen, methyl or ethyl;
$R^2_4$ is a group of formula (IV):

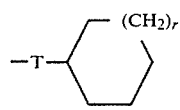

wherein:
T is a bond, or a $C_{1-6}$ alkylene group which may be straight chain or branched by one or two methyl groups at the same or different carbon atoms; and r is 0 to 3;
and salts thereof.

In formula (III) suitably X is O.

$R^1_2$ is more suitably hydrogen or methyl, preferably methyl.

In formula (IV) often T will be a group $—(CH_2)_q—$ wherein q is 0 to 4. Also suitably r is 1.

Suitably $R_5$ is methyl or ethyl, preferably methyl.

It will of course be realised that the compounds of the formula (I) have asymmetric centres, and thus are capable of existing in a number of stereoisomeric forms. The invention extends to each of these stereoisomeric forms, and to mixtures thereof. The different stereoisomeric forms may be separated one from the other by the usual methods.

The present invention further provides a process for the preparation of the compounds of the formula (I), which process comprises the cyclisation of a compound of formula (V):

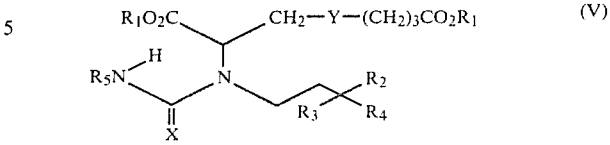

wherein:
Y is $—CH=CH—$ or $—C\equiv C—$;
$R_3$ is hydroxy or protected hydroxy; and the remaining groups are as defined; and thereafter as necessary in the thus formed compound converting Y being $—C\equiv C$ to $—CH=CH—$ and $R_3$ being protected hydroxy to hydroxy; and if desired or necessary converting $R_1$ into another variable $R_1$.

Suitable protected hydroxyl groups $R_3$ include readily hydrolysable groups such as acylated hydroxy groups in which the acyl moiety contains 1 to 4 carbon atoms, for example the acetoxy group; and hydroxy groups etherified by readily removable inert groups such as the benzyl group or like groups. Preferably $R_3$ is hydroxyl.

The compound of the formula (V) is conveniently prepared in situ during the reaction of a compound of the formula (VI):

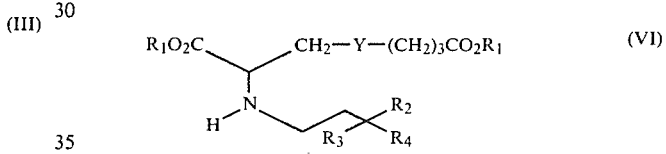

wherein:
Y, $R_1$, $R_2$, $R_3$ and $R_4$ are as defined, with $R_5NCX$, a preferred process of the invention.

This preferred process is suitably carried out under reflux in an inert solvent such as benzene or the like. It should be stated that when in this reaction $R_5$ is a sterically hindered group then this reaction may proceed only as far as the uncyclised compound of formula (V) in which case the necessary cyclisation of the compound (V) can be achieved with a strong base, such as sodium hydride or sodium ethoxide, in a dry organic solvent. Sodium ethoxide in benzene, or potassium t-butoxide in toluene, benzene or hexamethylphosphoramide are suitable reagents.

The present invention also provides a further process for the preparation of compounds of the formula (I), which process comprises the alkylation of a compound of the formula (VII):

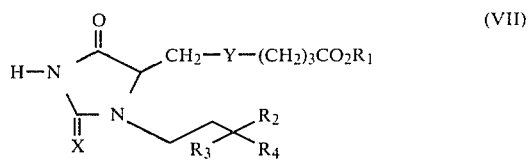

wherein the variables are as defined in formula (V), by conventional substitution reactions with $R_5L$ wherein $R_5$ is as defined in formula (I) and L is a good leaving group; and thereafter as necessary in the thus formed compound converting Y being $—C\equiv C—$ to $—CH=$-

CH— and Y being protected hydroxy to hydroxy. In such reactions it may be necessary to convert the compound of the formula (VII) first to an alkali metal salt at the 10-position (prostaglandin numbering).

Compounds of the formula (VII) may be prepared by the cyclisation of a compound of formula (VIII):

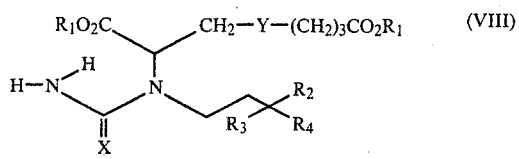

wherein: the variable groups are as defined; and thereafter if desired or necessary converting Y, $R_1$ or $R_3$ in the thus formed compound into other variable Y, $R_1$ or $R_3$.

When $R_1$ is hydrogen in the compound of formula (VIII), then the cyclisation may suitably be carried out in aqueous conditions at acid pH, for example in 25% aqueous acid.

Such compounds of the formula (VIII) can be prepared by reacting a salt $M^+$ $^-CNX$, wherein $M^+$ is a metal ion and X is O or S as defined, with a compound of formula (VI), wherein n, $R_1$, $R_2$, $R_3$ and $R_4$ are as defined. The metal salt thus obtained can be converted to the acid (VIII) with mineral acid. Suitably $M^+$ is a sodium or potassium ion, preferably a potassium ion.

When $R_1$ is other than hydrogen the compound of the formula (VIII) is conveniently formed in situ during the conversion of a compound of formula (VI) into a corresponding compound of the formula (VII) by reaction with $M^+$ $^-CNX$, a second preferred process of the invention. This conversion may suitably by achieved using a hydrochloride salt of the compound of the formula (VI) and reacting that salt with $M^+$ $^-CNX$ in aqueous solution at reflux or in aqueous dichloromethane with a phase transfer catalyst.

When the two $R_1$ groups in the compounds of formula (V) and (VIII) are other than hydrogen, they are preferably the same group.

The conversion of a compound of the formula (I) to another compound of the formula (I) wherein $R_1$ is altered, when desired or necessary, may be achieved in conventional manner, for instance by conventional esterification and/or de-esterification reactions.

Similarly, in a compound formed by the cyclisation of a compound of the formula (V) wherein Y is —C≡C— and/or $R_3$ is protected hydroxy and which is thus not of the formula (I) $R_1$ may be converted to another $R_1$ in the above manner. Analogously, in a compound formed by the alkylation of a compound of the formula (VIII) wherein Y is —C≡C— and/or $R_3$ is protected hydroxy, $R_1$ may also be altered in the above manner.

When Y in the above cyclisation and alkylation products is —C≡C—, these compounds may be reduced to compounds of the formula (I) in conventional manner. Suitably this reaction is carried out using catalytic hydrogenation, for example by Lindlar catalysis.

When $R_3$ in these products is protected hydroxy, compounds of the formula (I) may be produced by conventional deprotection reactions. For example when $R_3$ is a benzyloxy group, the benzyl group may readily be removed by acidic hydrolysis.

Thus it may be seen that such 'protected hydroxy' and 'alkynylene' products are useful intermediates in the preparation of the corresponding 'free hydroxy' and 'alkenylene' compounds of the formula (I).

Also when a compound of the formula (I) contains an acidic hydrogen atom(s), salts thereof may be prepared in conventional manner for example by reacting the compound of the formula (I) with the required base.

Preparation of Intermediates

The compounds of formula (VI) may be prepared by reacting a compound of formula (IX): $H_2NCH_2ch_2NR_2R_3R_4$ with a compound of formula (X): $R_1O_2C$—$CH(Q)$—$CH_2$—Y— $(CH_2)_3CO_2R_1$, wherein the variable groups are as defined and Q is a good leaving group.

Suitably Q is tosylate or a halide, or like readily displaceable group. Preferably Q is bromide.

This displacement reaction occurs under conventional conditions, for example in an organic solvent in the presence of a base. The reaction may suitably be carried out in hexamethylphsphoramide in the presence of sodium carbonate and sodium iodide at ambient temperature or below.

Compounds of formula (IX) may be prepared in known manner.

Compounds of formula (X) may suitably be prepared by de-acylation of a corresponding compound of the formula (XI):

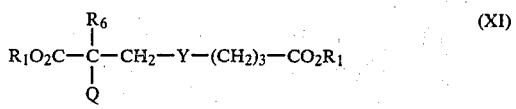

wherein $R_6$ is an acyl group containing up to 6 carbon atoms (preferably acetyl).

This de-acylation can conveniently be carried out by reaction with a suspension of anhydrous barium hydroxide in alcohol at 0° C.

Compounds of the formula (XI) may be prepared by substitution of a corresponding compound of the formula (XII):

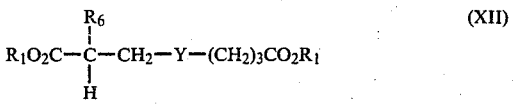

with a good leaving group.

This reaction is suitably carried out in an organic solvent such as tetrahydrofuran in the presence of a strong base such as sodium hydride. When Q is bromide in the desired compound of formula (XI), the reaction is suitably carried out with bromine dissolved in a suitable organic solvent such as dichloromethane, at ambient temperature or below.

Compounds of formula (XII) may be prepared from compounds of the formula (XIII): $R_1O_2C$—$CH_2$—$R_6$ by alkylation thereof with a compound of formula (XIV): Q—$CH_2$—Y—$(CH_2)_3CO_2R_1$.

This alkylation reaction can be carried out in conventional manner, for example in an organic solvent in the presence of a strong base such as sodium hydride at ambient temperature or below.

It is believed that compounds of the formula (VI) wherein Y is —C≡C—, and compounds of the formula (VI) wherein Y is —CH═CH— and $R_4$ is other than $C_{1-9}$ alkyl, are novel compounds, and as such form an important part of this invention.

In an alternative synthetic route, the compounds of the formula (VI) may be prepared by a process which comprises reacting a compound of formula (XV):

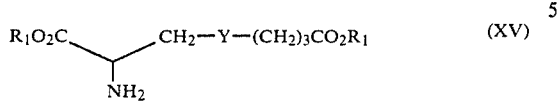
(XV)

with a compound of formula (XVI):

(XVI)

This reaction is suitably carried out in an inert organic solvent, such as hexamethylphosphoramide or N,N-dimethylformamide, at room temperature, in the presence of a base, such as sodium carbonate or sodium hydride, and a source of alkali metal ions, such as an alkali metal halide. Suitable alkali halides include sodium iodide and lithium iodide.

The compounds of formula (XV) may suitably be prepared by cleavage of a compound of formula (XVII):

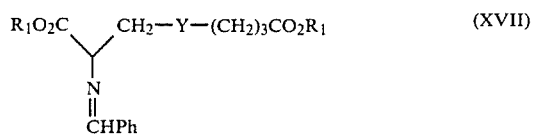
(XVII)

Suitably this cleavage is carried out with mild acid catalysis, for example by chromatography on acid washed silica gel.

These compounds of formula (XVII) can be prepared by reaction of a compound of formula (XVIII):

(XVIII)

with a compound of formula (XIV) Q—CH$_2$—Y—(CH$_2$)$_3$CO$_2$R$_1$ (as hereinbefore defined) in normal manner for such alkylation reactions, for example as hereinbefore described.

In a variation of this alternative synthetic route, the compounds of formula (XV) may be prepared by hydrolysis of the corresponding nitrile of formula (XIX):

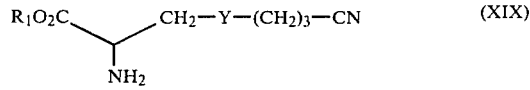
(XIX)

to give a compound of the formula (XV) wherein both R$_1$ groups are hydrogen, and thereafter if desired or necessary esterifying these R$_1$ hydrogen groups.

The hydrolysis may be carried out in known manner for such reactions.

The compounds of formula (XIX) may be prepared by reacting a compound of formula (XX):

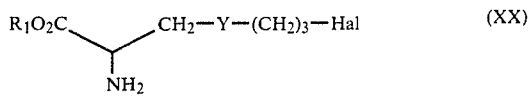
(XX)

wherein Hal is a halide, preferably bromide, with an inorganic cyanide, such as NaCN, in an organic solvent such as DMSO.

In turn, the compounds of formula (XX) may themselves be prepared by substitution of a compound of formula (XVIII) as defined with a compound of formula (XXI):

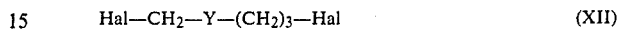
Hal—CH$_2$—Y—(CH$_2$)$_3$—Hal (XII)

(wherein the two Hal atoms are not necessarily the same), in known manner as herein discussed.

The compounds of formula (XXI) are suitably prepared by halogenation of a compound of formula (XXII) HO—CH$_2$—Y—(CH$_2$)$_3$—Hal (for example by reaction with PBr$_3$), which is in turn suitably prepared from a compound of formula (XXIII):

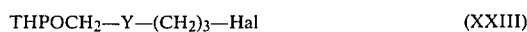
THPOCH$_2$—Y—(CH$_2$)$_3$—Hal (XXIII)

wherein THP is a tetrahydropyranyl radical, by acid catalysed cleavage.

In a further variation of the alternative synthesis, the compound of formula (XV) may be prepared by hydrolysis and partial decarboxylation of a compound of formula (XXIV)

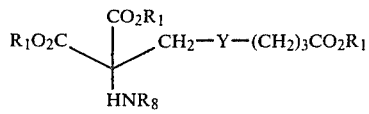

wherein R$_8$ is CHO or COR$^1$$_8$ wherein R$^1$$_8$ is C$_{1-4}$ alkyl, preferably methyl, and subsequent optional esterification of the CO$_2$R$_1$ acid groups.

This hydrolysis and partial decarboxylation is suitably carried out in the presence of strong acid.

The compounds of formula (XXIV) may be prepared by substituting a compound of formula (XXV):

(XXV)

with a compound of formula (XIV) as hereinbefore defined, in the usual manner.

Compounds of the formula (I) have useful pharmacological activity. For example compounds within the formula (I) have anti-gastric secretion activity, e.g. anti-ulcer activity, cardiovascular activity e.g. antihypertensive activity, platelet aggregation inhibition activity, affect the respiratory tract, e.g. bronchodilator activity, and have anti-fertility, smooth muscle and anti-arrhythmic activity.

The compounds of the formula (I) are especially useful as bronchodilation agents.

In general it may be said that compounds within the formula (I) have a range of pharmacological activities similar to those shown by the natural prostaglandins, but that these activities tend to be rather more selective.

The invention therefore also provides a pharmaceutical composition comprising a compound of the formula (I) and a pharmaceutically acceptable carrier.

The compounds of the formula (I) also have a good stability.

Clearly the formulation of the said pharmaceutical composition will depend on the nature of the activity shown by the chosen compound of the formula (I), and on other factors such as a preference in a particular area of therapy for a particular mode of administration.

The composition may be in the form of tablets, capsules, powders, granules, lozenges or liquid preparations, such as oral or sterile parenteral solutions or suspensions.

Tablets and capsules for oral administration may be in unit dose presentation form, and may contain conventional excipients such as binding agents, fillers, tabletting lubricants, disintegrants, and acceptable wetting agents and the like. The tablets may be coated according to methods well known in normal pharmaceutical practice. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, emulsifying agents, non-aqueous vehicles (which may include inedible oils), preservatives, and if desired conventional flavouring or colouring agents, and the like.

For parenteral administration, fluid unit dosage forms are prepared utilising the compound of the formula (I) and a sterile vehicle. The compound, depending on the vehicle and concentration used, can be either suspended or dissolved in the vehicle. In preparing solutions the compound can be dissolved for injection and filter sterilised before filling into a suitable vial or ampoule and sealing. Advantageously, adjuvants such as a local anaesthetic, preservatives and buffering agents can be dissolved in the vehicle. Parenteral suspensions are prepared in substantially the same manner except that the compound is suspended in the vehicle instead of being dissolved and sterilisation cannot be accomplished by filtration. The compound can be sterilised by exposure to ethylene oxide before suspending in the sterile vehicle. Advantageously, a surfactant or wetting agent is included in the composition to facilitate uniform distribution of the compound.

When appropriate, the compositions of this invention may be presented as an aerosol for oral administration, or as a microfine powder for insufflation.

As is common practice, the compositions will usually be accompanied by written or printed directions for use in the medical treatment concerned.

It will of course be realised that the precise dosage used in the treatment of any of the hereinbefore described disorders will depend on the actual compound of the formula (I) used, and also on other factors such as the seriousness of the disorder being treated.

The invention also provides a method of treatment and/or prophylaxis of disorders in human beings or animals which comprises the administration to the sufferer of an effective amount of a compound of the formula (I). Normally the compounds will be used in the therapy of human disorders.

The following Examples illustrate the preparation of compounds of the formula (I) and their pharmacological properties, and the following Descriptions illustrate the preparation of intermediates thereto:

DESCRIPTION 1

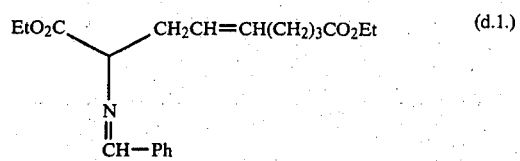

The N-benzylidene derivative of glycine ethyl ester prepared as described by G. Stork, et al J. Org. Chem., 41, 3491 (1976) (3.82 g, 0.02 mole) in dry tetrahydrofuran (15 ml) was added dropwise to a stirred suspension of potassium t-butoxide (2.24 g, 0.02 mole) in dry tetrahydrofuran (50 ml) under nitrogen at $-78°$. The solution immediately became bright red in colour.

After 30 minutes, sodium iodide (0.5 g) was added to the solution, followed by the dropwise addition of ethyl 7-bromo-hept-5-enoate (4.70 g, 0.02 mole). The solution became pale yellow in colour as it was allowed to warm up to room temperature over 2 hours. The solution was stirred for a further 5 hours at room temperature. Saturated ammonium chloride solution (50 ml) was added, and the organic layer was extracted with ether, washed with brine (2×100 ml), dried ($Na_2SO_4$) and evaporated in vacuo below 30° to give ethyl 2-(benzylideneamino)-8-ethoxycarbonyl-oct-4-enoate (5 g) as an orange oil.

| N.M.R. ($\tau$) CCl4. | 1.75 (S, 1H, N=CH—Ph) |
|---|---|

In similar manner was prepared compound (d.2): ethyl 2-(benzylideneamino)-8-ethoxycarbonyl-oct-4-ynoate

| N.M.R. ($\tau$) CCl$_4$ | 1.7 (s, 1H, N=CH—Ph) |
|---|---|

DESCRIPTION 2

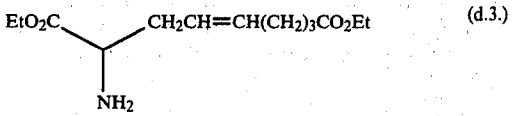

Ethyl 2-(benzylideneamino)-8-ethoxycarbonyl-oct-4-enoate (d.1) (5 g.) was passed through acid-washed silica gel (Merck:Kieselgel 60) (50 g.) After elution of benzaldehyde with pentane, eultion with 95% ether/5% methanol gave ethyl 2-amino-8-ethoxycarbonyloct-4-enoate (2.5 g) as a colourless oil.

| I.R. ($cm^{-1}$) Film | 3400, 1600 [$NH_2$], 1730 [$CO_2Et$] |
|---|---|
| N.M.R. ($\tau$) CDCl$_3$ | 4.6 (m, 2H, CH=CH) |
| | 5.8 (q, J = 7Hz, 2H, $CO_2CH_2CH_3$) |
| | 5.9 (q, J = 7Hz, 2H, $CO_2CH_2CH_3$) |
| | 6.5 (t, J = 7Hz, 1H, N—CH) |
| | 7.4–8.5 (brm, 8H, $CH_2CH=CHCH_2CH_2CH_2CO_2Et$) |
| | 8.35 (s, 2H, $NH_2$) |
| | 8.7 (t, J = 7Hz, 3H, $CO_2CH_2CH_3$) |

8.7 (t, J = 7Hz, 3H, CO₂CH₂CH₃)

In a similar manner compound (d.4) ethyl 2-amino-8-ethoxycarbonyl-oct-4-ynoate was prepared from compound (d.2).

| I.R. (cm⁻¹) film | 3400, 1600 [NH₂]; 1730 [CO₂Et] |
|---|---|
| N.M.R. (τ) CDCl₃ | 5.8 (q, J = 7Hz, 2H, CO₂CH₂CH₃) |
| | 5.9 (q, J = 7Hz, 2H, CO₂CH₂CH₃) |
| | 6.55 (t, J = 7H, 1H, N—CH) |
| | 7.4–8.5 (brm, 8H, CH₂C≡CCH₂CH₂CH₂CO₂Et) |
| | 8.1 (s, 2H, NH₂) |
| | 8.7 (t, J = 7Hz, 3H, CO₂CH₂CH₃) |
| | 8.7 (t, J = 7Hz, 3H, CO₂CH₂CH₃) |
| Analysis | C₁₃H₂, NO₄ |
| Requires | C, 61.16, H, 8.29; N 5.49% |
| Found | C, 61.11; H, 7.96; N, 5.27% |

DESCRIPTION 3

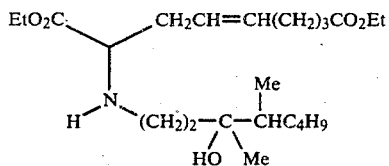
(d.5)

To a solution of ethyl 2-amino-8-ethoxycarbonyl-oct-4-enoate (d.3) (5.5 g, 0.021 mole) in hexamethylphosphoramide (20 ml) was added sodium carbonate (3.2 g, 0.03 mole), sodium iodide (2 g, 0.014 mole) and 1-(p-toluenesulphonyl)-3,4-dimethyloctan-3-ol (8.17 g. 0.023 mole) in hexamethylphosphoramide (20 ml), and the resultant mixture was stirred at room temperature for 70 hours.

The reaction mixture was then poured into water (200 ml) and extracted with ether (3×200 ml). The combined organic extracts were washed with water (3×200 ml) and saturated sodium chloride solution (3×200 ml), dried (Na₂SO₄) and evaporated in vacuo to give an orange oil (11 g). This was chromatographed on silica gel (300 g) using chloroform as eluant to give ethyl 8-ethoxycarbonyl-2-[N-(3'-hydroxy-3'-methyl-4'-methyl-n-octyl)-amino]-oct-4-enoate (4.1 g) as a yellow oil.

| I.R. (cm⁻¹) film | 3.300 [OH,NH], 1730 [CO₂Et] |
|---|---|

The compounds shown in Table 1 were prepared in a similar manner.

TABLE 1

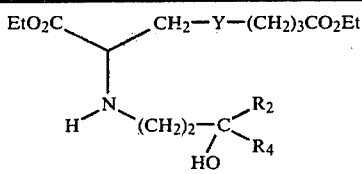

| Compound Number | Y | R₂ | R₄ |
|---|---|---|---|
| (d.6) | CH=CH | CH₃ | C₆H₁₃ |

TABLE 1-continued

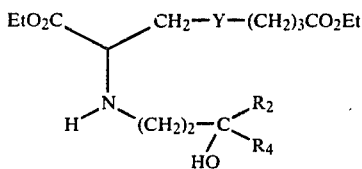

| | Y | R₂ | R₄ |
|---|---|---|---|
| (d.7) | C≡C | CH₃ | C₆H₁₃ |
| (d.8) | C≡C | |  |

| Compound (d.7) | |
|---|---|
| Analysis: | C₂₃H₄,NO₅ |
| Requires: | C,67.12; H,10.04; N,3.40% |
| Found: | C,67.10; H,10.13; N,3.62% |
| Mass Spectrum: | C₂₃H₄₂NO₅ [M⁺ + H] |
| requires | 412.3060 |
| found | 412.3092 |

DESCRIPTION 4

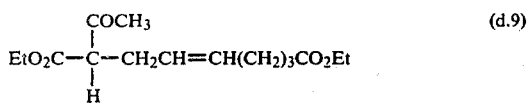
(d.9)

Ethyl acetoacetate (13 g; 0.1 mole) in dry tetrahydrofuran (30 ml) was added to a stirred suspension of sodium hydride (3.1 g; 0.11 mole; 80% oil dispersion) in dry tetrahydrofuran (50 ml), under nitrogen, at room temperature. The mixture was stirred for 1 hour. Sodium iodide (1.6 g; 0.01 mole) was then added to the mixture, followed by the dropwise addition of ethyl 7-bromo-hept-5-enoate (23.5 g; 0.1 mole) in dry tetrahydrofuran (100 ml.). The mixture was stirred for 24 hours at room temperature.

The mixture was partitioned between water and ether. The ether solution was washed with brine (2×200 ml), dried (Na₂SO₄) and evaporated in vacuo to give ethyl 9-oxo-8-ethoxycarbonyl-dec-5-enoate as a colourless oil (24 g.)

| N.M.R. (γ) CDCl₃ | 7.8 (S, 3H,CH₃CO) |
|---|---|

DESCRIPTION 5

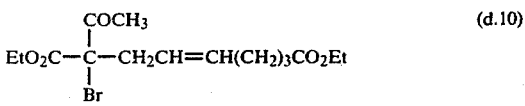
(d.10)

Ethyl 9-oxo-8-ethoxycarbonyl dec-5-enoate (d.9) (24 g; 0.088 mole) in dry tetrahydrofuran (100 ml) was added to a stirred suspension of sodium hydride (3 g; 0.1 mole; 80% oil dispersion) in dry tetrahydrofuran (50 ml), under nitrogen, at room temperature. The mixture was stirred for 1 hour, and then cooled to −10°, using an ice-salt bath. Bromine (2.3 ml; 0.09 mole) in dry dichloromethane (60 ml) was then added rapidly. The mixture was stirred for 30 minutes and then partitioned between water and ether. The ether solution was washed with brine (2×200 ml), dried (Na₂SO₄) and evaporated in vacuo, to give an orange oil (25 g). The oil was chromatographed on silica gel (500 g) using chloroform as eluant to give ethyl 9-oxo-8-bromo-8-ethoxycarbonyl dec-5-enoate (12.5 g) as a pale yellow oil.

| N.M.R. (τ) (CDCl₃) | 7.6 (s,3H,CH₃CO) |
|---|---|

DESCRIPTION 6

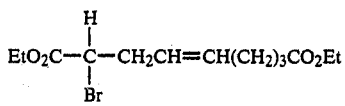 (d.11)

Anhydrous barium hydroxide (3.06 g; 0.018 mole) was added portionwise to a stirred solution of ethyl 9-oxo-8-bromo-8-ethoxycarbonyl-dec-5-enoate (d.10) 12.5 g; 0.036 mole) in dry ethanol at 0°. The suspension was stirred for 30 minutes. The mixture was filtered and the alcohol filtrate partitioned between ether and brine. The ether solution was washed with brine (2×100 ml), dried (Na₂SO₄) and evaporated in vacuo to give a brown oil (11 g). The oil was chromatographed on silica gel (300 g.) using chloroform as eluant to give ethyl 2-bromo-8-ethoxycarbonyl-oct-4-enoate (8 g) as a pale yellow oil.

| I.R. (cm⁻¹) Film | 1730 [CO₂Et] |
|---|---|
| N.M.R. (τ) (CDCl₃) | 4.6 (br m, 2H, CH=CH) |
| | 5.8 (br m, 5H, 2 × CO₂CH₂CH₃,CH—Br) |
| | 7.15 (m, 2H, CH₂CH=CH) |

DESCRIPTION 7

Alternative synthetic route for (d.6)

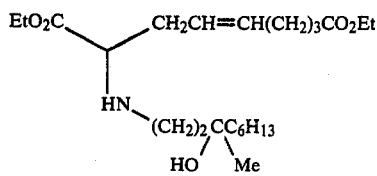 (d.6)

Ethyl 2-bromo-8-ethoxycarbonyl-oct-4-enoate (d.11) (3.21 g; 0.01 mole) in HMPA (10 ml) was added dropwise to a stirred solution of 3-hydroxy-3-methyl nonylamine (1.73 g; 0.01 mole) in HMPA (20 ml) containing anhydrous sodium carbonate (1.6 g; 0.015 mole) and sodium iodide (0.16 g; 0.001 mole) at −10°. The mixture was stirred between −10° and 20° for 2 hours and at room temperature for 16 hours.

The mixture was partitioned between brine and ether. The ether extract was washed with brine (2×50 ml), dried (Na₂SO₄) and evaporated in vacuo to give a brown oil (3.2 g). The oil was chromatographed on silica gel (100 g) using chloroform as eluant to give ethyl-8-ethoxycarbonyl-2-[N-(3'-hydroxy-3'-methyl-n-nonyl)-amino]-oct-4-enoate (1.2 g) as a yellow oil.

EXAMPLE 1

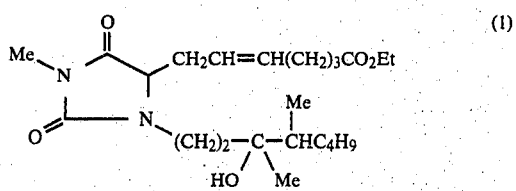 (1)

Ethyl 8-ethoxycarbonyl-2-[N-(3'-hydroxy-3'-methyl-4'-methyloctyl)-amino]-oct-4-enoate (d5) (4.1 g, 0.01 mole) was refluxed with methyl isocyanate (0.65 g, 0.011 mole) for 3 hours in dry toluene (100 ml). The toluene was evaporated in vacuo to give a pale yellow oil (4 g). This was chromatographed on silica gel (150 g) using chloroform as eluant to give 1-(3'-hydroxy-3'-methyl-4'-methyl-n-octyl)-3-methyl-5-(6''-ethoxycarbonyl-n-hex-2''-enyl)-hydantoin (3.0 g) as a pale yellow oil.

| I.R. (cm⁻¹): | 3450 [OH], |
|---|---|
| | 1760, 1700 [—N—C—N—C—] ‖ ‖ O O |
| | 1730 [CO₂Et]. |
| NMR (τ) (CDCl₃) | 8.1 to 7.2 (brm, 6H, CH₂—CH=CH₂—CH₂CO₂H), |
| | 7.0 (s, 3H, N—CH₃), |
| | 6.8 to 6.1 (brm, 2H, N—CH₂), |
| | 5.9 (q, 2H, CO₂CH₂), |
| | 5.9 (t, 1H, N—CH), |
| | 4.6 (brm, 2H, CH=CH). |

The compound shown below was prepared in a similar manner from (d.6) (prepared by the methods of Description 3 or Description 7):

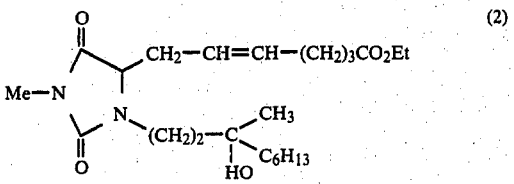 (2)

1-(3'-hydroxy-3'-methyl-n-octyl)-3-methyl-5-(6''-ethoxycarbonyl-n-hex-2''-enyl)-hydantoin

| IR (cm⁻¹) Film | 3450 [OH] |
|---|---|
| | 1760, 1700 [—N—C—N—C—] ‖ ‖ O O |
| | 1730 [CO₂Et] |
| NMR (τ) | 4.6 (brm, 2H, CH=CH) |
| | 5.9 (q, 2H, CO₂CH₂CH₃) |
| | 5.9 to 6.9 (brm, 3H, N—CH₂, N—CH) |
| | 7.0 (s, 3H, N—CH₃), |
| | 7.2 to 8.2 (brm, 6H, CH₂—CH—CH—CH—CH₂,CH₂CO₂H) |

EXAMPLE 2

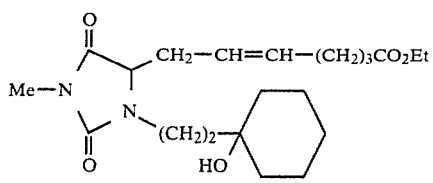
(3)

1-[2'-(1''-hydroxycylohexyl)ethyl]-3-methyl-5-(6'''-ethoxycarbonylhex-2'''-enyl)hydantoin, (3) was prepared as follows:

(a) The compound shown below was prepared in a similar manner to that of Compound 1 of Example 1.

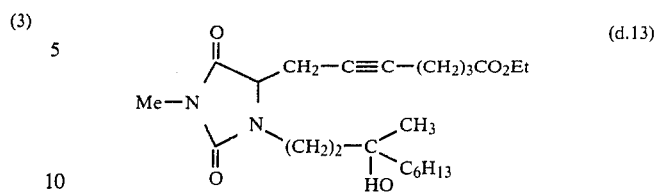
(d.12)

| I.R (cm$^{-1}$): | 3450 [OH] |
|---|---|
| | 1770, 1710 [—N—C—N—C—] |
| | ‖  ‖ |
| | O  O |
| | 1730 [CO$_2$Et] |
| NMR ($\tau$) | 5.85 (q, 2H, CO$_2$CH$_2$CH$_3$) |
| | 5.9 to 6.8 (brm, 3H, N—CH$_2$, N—CH) |
| | 7.0 (s, 3H, N—CH$_3$) |
| | 7.2 (m, 2H, CH$_2$—C≡C). |
| Mass spectrum: | C$_{21}$H$_{32}$N$_2$O$_5$ (M$^+$) |
| requires: | 392.2309 |
| found: | 392.2312 |

(b) A solution of 1-[2'-(1''-hydroxycyclohexyl)ethyl]-3-methyl-5-(6'''-ethoxycarbonyl-n-hex-2'''-ynyl)hydrantoin (d12) (0.7 g) in dry ethanol (20 ml) was added to a suspension of 5% palladium on calcium carbonate (70 mg) in ethanol (10 ml) containing quinoline (0.5 ml).

The mixture was hydrogenated at atmospheric pressure at 25° for 5 hours. The mixture was filtered through kieselguhr and evaporated in vacuo. The residual oil was partitioned between ether and 1 N hydrochloric acid. The organic phase was separated and was washed with brine (2×50 ml), dried (MgSO$_4$) and evaporated in vacuo, to give a yellow oil. This was chromatographed on silica gel (50 g) using chloroform as eluant to give 1-[2'-(1''-hydroxycyclohexyl)ethyl]-3-methyl-5-(6''-ethoxycarbonyl-n-hex-2'''-enyl)hydantoin (0.4 g) as a pale yellow oil.

| I.R (cm$^{-1}$): | 3450 [OH], |
|---|---|
| Film | 1760, 1700 [—N—C—N—C—] |
| | ‖  ‖ |
| | O  O |
| | 1730 [CO$_2$Et] |
| NMR | 4.6 (brm, 2H, CH=CH) |
| | 5.85 (q, 2H, CO$_2$CH$_2$CH$_3$) |
| | 5.9 to 6.8 (brm, 3H, N—CH$_2$,N—CH) |
| | 7.0 (s, 3H, N—CH$_3$) |
| Mass spectrum: | C$_{21}$H$_{34}$N$_2$O$_5$ (M$^+$) |
| requires: | 394 2467 |
| found: | 394 2474 |

Compound 2 (which was also prepared by the method of Example 1) was prepared in a similar manner, as an alternative synthesis, by (a) the preparation of the compound shown below by the method of Example 1.

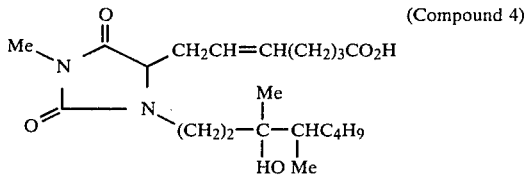
(d.13)

and (b) its subsequent partial hydrogenation.

| Compound (d13) | |
|---|---|
| I.R(cm$^{-1}$): | 3450 [OH] |
| film | 1760, 1700 [—N—C—N—C—] |
| | ‖  ‖ |
| | O  O |
| | 1730 [CO$_2$Et] |
| NMR ($\tau$) | 5.85 (q, 2H, CO$_2$CH$_2$CH$_3$) |
| | 5.9 to 6.9 (brm, 3H, N—CH$_2$, N—CH) |
| | 7.0 (s, 3H, N—CH$_3$) |
| | 7.2 (m, 2H, CH$_2$C≡C) |
| Analysis: | C$_{23}$H$_{33}$N$_2$O$_5$ |
| requires: | C, 65.38; H, 9.06; N, 6.63% |
| found: | C, 65.48; H, 9.09; N, 6.97% |

EXAMPLE 3

(Compound 4)

1-(3'-Hydroxy-3'-methyl-4'-methyl-n-octyl)-3-methyl-5-(6''-ethoxy-carbonyl-n-hex-2''-enyl)-hydantoin (1) (3 g) was refluxed for 16 hours with 10% aqueous potassium carbonate (30 ml) and ethanol (100 ml). The solvent was evaporated in vacuo, and the residual oil was partitioned between ether and water. The aqueous phase was acidified to pH 3 with 5 N HCl and extracted with ether. The etheral extract was washed with brine, dried (MgSO$_4$) and evaporated to vacuo to give 1-(3'-hydroxy-3'-methyl-4'-methyl-n-octyl)-3-methyl-5(6''-carboxy-n-hex-2''-enyl)hydantoin (2.2 g) as a pale yellow oil.

| I.R. (cm$^{-1}$): | 3600 to 2500 [CO$_2$H, OH], |
|---|---|
| | 1760, 1730 (broad) [—N—C—N—C—; |
| | ‖  ‖ |
| | O  O |
| | CO$_2$H]. |
| NMR ($\tau$): | 8.1 to 7.3 (brm, 6H, CH$_2$—CH=CH—CH$_2$—, |
| (CDCl$_3$) | CH$_2$CO$_2$H), |
| | 7.0 (s, 3H, N—CH$_3$), |
| | 6.8 to 6.1 (brm, 2H, N—CH$_2$), |
| | 5.9 (t, 1H, N—CH), |
| | 4.6 (brm, 2H, CH=CH), |
| | 3.9 (brs, 2H, OH, CO$_2$H). |
| Mass spectrum: | C$_{21}$H$_{34}$N$_2$O$_4$ [M$^+$—H$_2$O] |
| | requires: 378.2519 |
| | found: 378.2480 |
| Analysis: | C$_{21}$H$_{36}$N$_2$O$_5$ |
| | required: C, 63.61; H, 9.15; |
| |    N, 7.06%. |
| | found: C, 63.35; H, 9.44; |

N, 7.17%.

The compounds shown in Table 3 were prepared in similar manner from compounds (2) and (3) respectively.

TABLE 3

| Compound Number | R2 | R4 |
|---|---|---|
| 5 | Me | C6H13 |
| 6 | | ⬡ |

Compound 5
I.R (cm⁻¹): 3700 to 2500 [CO2H; OH]
film          1770, 1730 (broad) [—N—C—N—C—;CO2H]
                                      ‖      ‖
                                      O      O
NMR (τ)       3.3 (br s, 2H, OH, CO2H)
(CDCl3)       4.5 (brm, 2H, CH=CH)
              5.9 (t, 1H, N—CH)
              6.1 to 6.8 (brm, 2H, N—CH2)
              7.0 (s, 3H, N—CH3)
              7.2 to 8.1 (brm, 6H, CH2CH=CHCH2, CH2CO2H)
Mass spectrum: C21H34N2O4 [M⁺—H2O]
requires:     378.2519
found:        378.2531

Compound 6
I.R (cm⁻¹)    3700 to 2500 [CO2H;OH]
film          1770, 1730 (broad) [—N—C—N—C—;
                                      ‖      ‖
                                      O      O
              CO2H]
NMR (τ)       3.6 (br s, 2H, CHCO2H)
              4.6 (brm, 2H, CH=CH)
              5.9 (t, 1H, N—CH)
              6.1 to 6.8 (brm, 2H, N—CH2)
              7.0 (s, 3H, N—CH3)
Mass spectrum: C19H30N2O5
requires:     366.2155
found:        366.2140

EXAMPLE 4

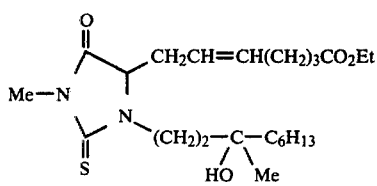
(7)

Ethyl 8-ethoxycarbonyl-2-[N-(3'-hydroxy-3'methyl-n-nonyl)-amino]-oct-4-enoate (d.12) (7.6 g) was refluxed with methyl iso-thiocyanate (1.35 g) in dry toluene (150 ml) for 3 hours. The toluene was evaporated in vacuo to give a yellow oil. This was chromatographed on silica gel (300 g) using chloroform as eluant to give 1-(3'-hydroxy-3'-methyl-n-nonyl)-5-(6''-ethoxycarbonyl-n-hex-2''-enyl)-2-thiohydantoin (3 g) as yellow oil.

I.R. (cm⁻¹)  3450 [OH]

Film         1750 to 1720 [—N—C—N—C— CO2Et]
                                ‖    ‖
                                S    O
N.M.R. (τ)   4.6 (brm, 2H, CH=CH)
(COCl3)      5.85 (q, 2H, CO2CH2CH3)
             5.9 to 7 (brm, 3H, N—CH2,N—CH)
             6.75 (s, 3H, N—CH2)
             7.3 (m, 2H, CH2CH=CH)
             7.8 (m, 3H, OH, CH2CO2Et)
Mass Spectrum   C23H40N2O4S (M⁺)
require         440,2707
found           440,2711

PHARMACOLOGICAL DATA

Bronchodilator activity

1. The compounds were examined for their ability to inhibit 5-hydroxytryptamine induced bronchoconstriction in the anaesthetised, artificially respired guinea pig (Konzett-Rossler preparation) The compounds were administered intravenously. The results are shown in Table A.

TABLE A

| Compound Number | ED50 against 5-hydroxytryptamine induced bronchoconstriction μg/kg i.v. |
|---|---|
| 4 | 0.6 |
| 5 | 1.3 |

2. The compounds were also examined for their ability to protect conscious guinea pigs against bronchoconstriction induced by a histamine aerosol (Herxheimer test). In these experiments the compounds were adminstered by aerosol. The results are shown in Table B.

TABLE B

| Compound Number | Activity (μg/ml) Aerosol administration |
|---|---|
| 4 | 0.5 |
| 5 | 1 |

Anti-platelet aggregation activity

The compounds were examined for their ability to inhibit platelet aggregation induced in vitro by collagen in human platelet rich plasma. The results are shown in Table C.

TABLE C

| Compound Number | IC50(μM) against collagen induced aggregation |
|---|---|
| 4 | 28 |
| 5 | 22 |

Anti-ulcer activity

Method
Anti-ulcer activity was assessed by the inhibition of indomethacin induced gastric damage in the rat according to the method of Eleghe (1974) Israeli J. Med. Sci. IO, 1451. Rats were starved overnight, given 15 mg/kg indomethacin subcutaneously and sacrificed 4 hours later. Stomachs were reflated with n.saline, cut along the greater curvature pinned out and scored for gastric damage by the following system.

Score 1-3—according to degree of erythema and slight haemorrhage.

Score 4-6—according to degree of mucosal erosion.
Score 7-9—according to depth of gastric damage.

Groups of 7 rats were used for each treatment and the test compound or vehicle were administered 30 minutes prior to giving the indomethacin. Dose of test compound was 100 mg/kg orally and control groups receiving vehicle only were set up simultaneously. Mean values for each treatment were obtained using the above scoring system and the Mann Witney test applied for significance of difference between the values obtained with the treatments.

Compared with vehicle only treatment, compound 4 reduced the mean ulcer score and therefore has significant anti-ulcer activity.

Vehicle control: Mean Score±S.E. of Mean 4.14±0.59

Test: Mean Score±S.E. of mean 0.43±0.20 (p<0.01)

Anti-arrhythmic Activity

Compound 5 was examined for its ability to increase the voltage required to produce arrhythmia in electrostimulation of the right ventricle in anaesthatised guinea pigs. The results as shown in Table D.

TABLE D

| Compound Number | Dose mg/ kg I.d. | % increase of voltage ± SEM |
|---|---|---|
| 5 | 32.0 | 43.0 ± 7.0 (p<0.5) |

Comparison testing

The test for bronchodilator activity used in 'Bronchodilator activity' method 1 above was used with three test animals for the comparison testing of Compound 5 against the compound 5-(6-carboxyhexyl)-1-(3-hydroxy-4,4-dimethyloctyl)hydantoin (A) highlighted in German Offenlegungsschrift No. 2724948 for its anti-bronchoconstriction activity. The results are shown in Table E.

TABLE E

| Compound | ED$_{50}$ (mean) μg/kg, i.v. |
|---|---|
| 5 | 1.2 |
| A | 24.6 |

These results clearly show that compound 5 is at least an order of magnitude more potent a bronchodilator than Compound A.

Toxicity

No toxic effects were observed during the tests reported above.

What we claim is:

1. A compound of the formula:

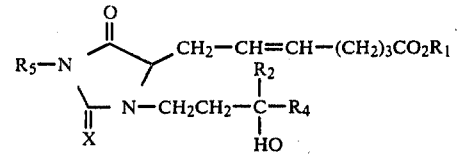

wherein
X is O or S;
$R_1$ is hydrogen, or $CO_2R_1$ represents an ester group in which $R_1$ contains from 1 to 12 carbon atoms;
$R_2$ is hydrogen or alkyl of 1 to 4 carbon atoms;
$R_4$ is alkyl of 1 to 9 carbon atoms; and
$R_5$ is alkyl of 1 to 6 carbon atoms; and the alkali metal, alkaline earth metal, ammonium and substituted ammonium salts thereof when $R_1$ is hydrogen.

2. A compound accord to claim 1 wherein X is O.
3. A compound according to claim 1 wherein $R_1$ is hydrogen or alkyl of 1 to 6 carbon atoms.
4. A compound according to claim 1 wherein $R_2$ is hydrogen, methyl or ethyl.
5. A compound according to claim 1 wherein $R_4$ is alkyl of 4 to 9 carbon atoms.
6. A compound according to claim 1 wherein $R_5$ is methyl or ethyl.
7. A compound according to claim 1 wherein:
$R_2$ is hydrogen, methyl or ethyl;
$R_4$ is alkyl of 1 to 9 carbon atoms; and salts thereof as therein defined.
8. A compound according to claim 7 wherein X is O.
9. A compound according to claim 7 wherein $R_2$ is methyl.
10. A compound according to claim 7 wherein $R_4$ is n-pentyl, n-hexyl or n-heptyl.
11. A compound according to claim 10 wherein $R_4$ is n-hexyl.
12. A compound according to claim 7 wherein $R_4$ is hex-2-yl, 2-methylhex-2-yl, hept-2-yl, 2-methylhept-2-yl, oct-2-yl or 2-methyloct-2-yl.
13. A compound according to claim 7 wherein $R_5$ is methyl.
14. 1-(3'-hydroxy-3'-methyl-n-nonyl)-3-methyl-5-(6''-carboxy-n-hex-2''-enyl)hydantoin.
15. 1-(3'-hydroxy-3'-methyl-4'-methyl-n-octyl)-3-methyl-5-(6''-carboxy-n-hex-2''-enyl)hydantoin.

* * * * *